(12) United States Patent
Negele et al.

(10) Patent No.: US 6,248,836 B1
(45) Date of Patent: Jun. 19, 2001

(54) AMPHIPHILIC GRAFT POLYMERS BASED ON GRAFT BASES CONTAINING N—VINYLCARBOXYLIC ACID UNITS, PROCESS FOR THEIR PREPARATION AND THEIR USE

(75) Inventors: Anton Negele, Deidesheim; Martin Rübenacker, Altrip; Jens Utecht, Neuluβheim; Hubert Meixner, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/319,659

(22) PCT Filed: Nov. 28, 1997

(86) PCT No.: PCT/EP97/06652

§ 371 Date: Jun. 10, 1999

§ 102(e) Date: Jun. 10, 1999

(87) PCT Pub. No.: WO98/25981

PCT Pub. Date: Jun. 18, 1998

(30) Foreign Application Priority Data

Dec. 10, 1996 (DE) ................................ 196 51 243

(51) Int. Cl.⁷ .................... C08F 271/00; C08F 271/02
(52) U.S. Cl. ............... 525/242; 525/326.9; 525/328.2
(58) Field of Search ................. 525/242, 326.9, 525/328.2

(56) References Cited

U.S. PATENT DOCUMENTS 4,167,597  9/1979  Yoshida et al. .
5,554,261  9/1996  Nilz et al. .

FOREIGN PATENT DOCUMENTS 27 11 458     9/1977   (DE) .
1 551 513     8/1979   (GB) .
WO 94/08092   4/1994   (WO) .
WO 95/25759   9/1995   (WO) .

*Primary Examiner*—Jeffrey Mullis
(74) *Attorney, Agent, or Firm*—Oblon, Spivak, McClelland, Maier & Neustadt, P.C.

(57) ABSTRACT

Amphiphilic graft copolymers are prepared by grafting a pre-formed graft base polymer comprising at least 5% by weight of units of formula (I)

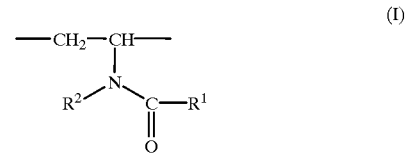

where R1 and R2 are independently H or $C_1$ to $C_6$ alkyl groups. The monomer grafted to the pre-formed graft base polymer is at least one of styrene or a $C_1$ to $C_2$ alkylstyrene, and optionally other monoethylenically unsaturated monomers. At least 5 mole % of the groups

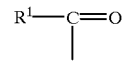

are cleaved from the grafted copolymer thus formed.

11 Claims, No Drawings

AMPHIPHILIC GRAFT POLYMERS BASED ON GRAFT BASES CONTAINING N—VINYLCARBOXYLIC ACID UNITS, PROCESS FOR THEIR PREPARATION AND THEIR USE

The invention relates to amphiphilic graft polymers based on graft bases containing N-vinylcarboxamide units, to processes for their preparation and to their use as strength enhancers for paper, as fixing agents for water-soluble and water-insoluble contaminants in papermaking, as an additive to detergents and cleaning products, as dispersants for organic and inorganic pigments, dyes, concrete and crop protection agents, as coating material for fertilizers and crop protection agents, as floor care agents, as a protective colloid for aqueous polymer dispersions, as thickeners for cosmetics formulations, as conditions for skincare compositions and as a constituent of cosmetic hair preparations and of cosmetic preparations for oral care.

DE-A-27 11 458 discloses a method of improving the keeping properties of a protective antidecay film, over which film a protective coating is applied by applying a composition comprising a polymer that has been prepared by polymerizing at least one vinyl monomer from the group consisting of methacrylates, acrylates, acrylonitrile, styrene, α-methylstyrene and vinyl acetate in the presence of a hydrophilic polymer from the group consisting of polyvinyl alcohol, polyethylene glycol, polypropylene glycol, polyvinylpyrrolidone and polyvinylamine. The graft polymers are prepared by free-radically initiated poly-merization of the monomers in the presence of said polymers in an organic solvent such as toluene.

U.S. Pat. No. 4,238,579 discloses copolymers comprising units of both vinylamine and styrene. They are prepared by free-radically initiated copolymerization of vinylacetamide and styrene in bulk or in solution with subsequent partial or complete hydrolysis of the amide groups of the copolymerized N-vinylacetamide to form amino groups. The polymers are used, for example, as coating materials or as hardeners for epoxy resins.

WO-A-95/25759 discloses graft polymers of which the graft base is a polymer containing in each case at least 5% by weight of units of the formulae

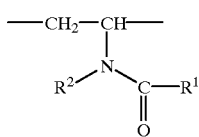

(I)

and/or

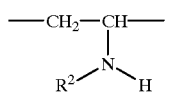

(II)

where $R^1$ and $R^2$ are H or $C_1$- to $C_6$-alkyl. Monoethylenically unsaturated monomers are grafted onto the graft base in a weight ratio of from 100:1 to 1:100.

The monomers grafted onto the graft base are preferably from the group consisting of N-vinylpyrrolidone, N-vinylcaprolactam, N-vinylimidazole, acrylic acid, methacrylic acid, acrylamide, acrylonitrile and vinyl acetate. The graft copolymers are used, for example, as dispersants for pigments, as an additive to detergents and cleaning products, as strength enhancers for paper and as materials for soil conditioning and fertilizer compaction.

Where the above-described graft copolymers are employed in papermaking, their effectiveness, and especially their fixing effect for soluble or insoluble papermaking contaminants, still leave something to be desired.

It is an object of the present invention to provide new graft polymers which especially in papermaking fix soluble and insoluble contaminants, such as pitch, effectively on the paper sheet that is formed.

We have found that this object is achieved, in accordance with the invention, with amphiphilic graft polymers based on graft bases containing N-vinylcarboxamide units, the amphiphilic graft polymers being obtainable by free radical polymerization of monomer mixtures of (a) styrene, a $C_1$- to $C_2$-alkylstyrene and/or vinyltoluene with or without (b) other monoethylenically unsaturated monomers copolymerizable therewith onto a polymer comprising at least 5% by weight of units of the formula

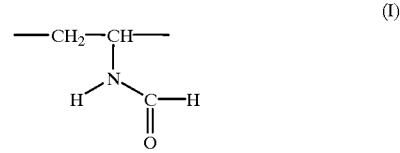

(I)

with or without units of the formula

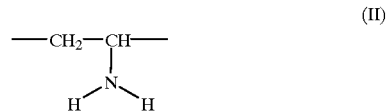

(II)

as graft base, in a weight ratio of from 1:99 to 99:1, and subsequent 5–100% cleavage of the formyl groups from the graft polymers, with the formation of amino groups.

The present invention also provides a process for preparing the abovementioned amphiphilic graft polymers, which involves subjecting monomer mixtures of (a) styrene, a $C_1$- to $C_2$-alkylstyrene and/or vinyltoluene with or without (b) other monoethylenically unsaturated monomers copolymerizable therewith to free-radical polymerization in the presence of polymers containing at least 5% by weight of N-vinylformamide units as graft base, in a weight ratio of from 1:99 to 99:1, and, after the graft polymerization, cleaving off from 5 to 100% of the formyl groups from the N-vinylformamide units, with the formation of amino groups.

The amphiphilic graft polymers described above are used with particular advantage as fixing agents for soluble and colloidal contaminants in papermaking. Examples of such contaminants are present in the pulp in the form of humic acids, ligninsulfonate, silicic acids or wood extract. The amphiphilic graft copolymers are used for fixing insoluble, lipophilic/hydrophobic contaminants, known as stickies or white pitch. They are also suitable as dispersants in the paper coating plant. Among the applications described above, their use as a protective colloid for acrylate, styrene and butadiene dispersions and as an additive to detergents and cleaning products is also of interest.

The graft base comprises polymers at least 5% by weight of whose copolymerized units are of the formula I above. Other suitable graft bases are hydrolyzed poly-N-vinylformamides which are obtainable by treating poly-N-vinylformamides with acids or bases and which in addition to the units of the formula I include units of the formula

(II)

The graft base can if desired contain up to 95% by weight of units of the formula II.

The units of the formula I are based on N-vinylformamide as the monomer. For polymer preparation these monomers can be used alone, in a mixture with one another, for example mixtures of N-vinylformamide and N-vinylacetamide, or together with other copolymerizable monomers. Processes for preparing such homo- and copolymers with other monomers are known, cf. EP-B-0 071 050, EP-B-0 215 387, EP-B-0 251 182, EP-A-0 528 409 and EP-A-0 337 310.

Examples of suitable other monomers which can be copolymerized with N-vinylformamide are monoethylenically unsaturated carboxylic acids with 3 to 8 carbons, such as acrylic, methacrylic, dimethacrylic, ethacrylic, maleic, citraconic, methylenemalonic, allylacetic, vinylacetic, crotonic, fumaric, mesaconic and itaconic acid. From this group of monomers it is preferred to use acrylic, methacrylic or maleic acid or mixtures thereof. The monoethylenically unsaturated carboxylic acids can be used in the form of free acid and—if in existence—the anhydrides, or in partially or completely neutralized form, in the copolymerization. To neutralize these monomers it is preferred to use alkali metal bases or alkaline earth metal bases, ammonia or amines, for example sodium hydroxide solution, potassium hydroxide solution, sodium carbonate, potash, sodium hydrogen carbonate, magnesium oxide, calcium hydroxide, calcium oxide, gaseous or aqueous ammonia, triethylamine, ethanolamine, diethanolamine, triethanolamine, morpholine, diethylenetriamine or tetraethylenepentamine.

Examples of other suitable comonomers for preparing the graft base are the esters, amides and nitriles of the abovementioned carboxylic acids, for example methyl and ethyl acrylates, methyl and ethyl methacrylates, hydroxyethyl, hydroxypropyl and hydroxybutyl acrylates, hydroxyethyl, hydroxypropyl and hydroxyisobutyl methacrylates, hydroxyisobutyl acrylate, monomethyl maleate, dimethyl maleate, monoethyl maleate, diethyl maleate, 2-ethylhexyl acrylate, 2-ethylhexyl methacrylate, acrylamide, methacrylamide, N,N-dimethylacrylamide, N-tert-butylacrylamide, acrylonitrile, methacrylonitrile, dimethylaminoethyl acrylate, diethylamino acrylate, diethylaminoethyl methacrylate, and also the salts of the latter monomers with carboxylic acids or mineral acids, and the quaternized products.

Other suitable copolymerizable monomers are acrylamidoglycolic acid, vinylsulfonic acid, allylsulfonic acid, methallylsulfonic acid, styrenesulfonic acid, 3-sulfopropyl acrylate, 3-sulfopropyl methacrylate and acrylamidomethylpropanesulfonic acid and also monomers containing phosphonic acid groups, such as vinylphosphonic acid, allylphosphonic acid and acrylamidomethanepropanephosphonic acid. These monomers containing acid groups can also be employed in the form of the free acids or else in partially or completely neutralized form. Suitable bases for neutralization have already been specified. It is preferred to employ sodium hydroxide solution or ammonia.

Other suitable compounds which can be copolymerized with N-vinyl formamide are N-vinylpyrrolidone, N-vinylcaprolactam, N-vinylimidazole, N-vinyl-2-methylimidazole, N-vinyl-4-methyl-imidazole, diallylammonium chloride, vinyl acetate and vinyl propionate. It is of course also possible to employ mixtures of these monomers.

The copolymers employed as graft base contain at least 5% by weight, usually at least 20% by weight and, with preference, at least 50% by weight of copolymerized N-vinylamides.

The copolymers employed as graft base are prepared by known techniques, for example solution, precipitation, suspension or emulsion polymerization using compounds which form free radicals under the polymerization conditions. The polymerization is generally carried out at from 30 to 200° C., preferably from 40 to 110° C. Examples of suitable initiators are azo and peroxycompounds and also the customary redox initiator systems, such as combinations of hydrogen peroxide and reductive compounds, for example sodium sulfite, sodium bisulfite, sodium formaldehyde sulfoxylate and hydrazine. These systems may possibly also include small amounts of a heavy metal salt.

The homopolymers and copolymers of N-vinylcarboxamides have K values of from at least 7 to 300, preferably from 10 to 250. The K values are determined in accordance with H. Fikentscher, Cellulose-Chemie, Volume 13, 58 to 64 and 71 to 74 (1932) in aqueous solution at 25° C. and at concentrations of from 0.1% to 5% depending on the K value range. By partly cleaving off the group

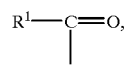

where $R^1$ is H, from the abovementioned homopolymers and copolymers, to form amine or ammonium groups, unhydrolyzed or hydrolyzed copolymers are obtained which contain units of the formula I and II and are to be used as the graft base. If hydrolyzed copolymers of the N-vinylcarboxamides are employed as graft base, the comonomers employed can also be modified chemically depending on the chosen hydrolysis conditions; for example, vinyl acetate units give vinyl alcohol units, methyl acrylate units give acrylic acid units, and acrylonitrile units give acrylamide or acrylic acid units.

Suitable hydrolyzing agents are mineral acids, such as hydrogen halides, which can be employed in gaseous form or in aqueous solution. It is preferred to use hydrochloric acid, sulfuric acid, nitric acid and phosphonic acid and also organic acids, such as $C_1$- to $C_5$-carboxylic acids and aliphatic or aromatic sulfonic acids. For each formyl group equivalent which can be cleaved off from the copolymerized units I it is possible to employ, for example, from 0.05 to 2, preferably from 1 to 1.5, mole equivalents of an acid.

The copolymerized units of the structure I can also be hydrolyzed using bases, for example metal hydroxides, especially alkali metal hydroxides and alkaline earth metal hydroxides. Preference is given to the use of sodium hydroxide or potassium hydroxide. Hydrolysis can also if desired be conducted in the presence of ammonia or amines. The vinylamine units can be employed for grafting in the form of free amines or as ammonium salts.

The above-described polymers containing units of the formula I and, if desired, II are subjected to grafting with styrene, alkylstyrenes and/or vinyltoluene. After the grafting reaction the resulting graft polymer is subsequently hydrolyzed under the conditions set out above. Subsequently, depending on the hydrolysis conditions, there are functional groups of the formula I and/or II.

Grafting is preferably carried out using styrene, an alkylstyrene, such as α-methylstyrene and α-ethylstyrene, and/or vinyltoluene as a nonhydrolyzable and hydrophobic monomer. It is of course also possible to employ mixtures of styrene and/or α-alkylstyrenes and/or vinyltoluene with all of the monomers that are suitable for grafting and have already been specified in WO-A-95/25759. These monomers are listed above as examples of comonomers for the preparation of the graft base. Preferred among these are acrylonitrile, n-butyl acrylate, n-butyl methacrylate, dimethylaminoethyl acrylate or 2-ethylhexyl acrylate.

Preference is given to those amphiphilic graft polymers which are obtainable by grafting, onto a graft base comprising a homopolymer of N-vinylformamide or a copolymer of N-vinylformamide and N-vinylcaprolactam, monomer mixtures of (a) from 5 to 100% by weight of styrene, a $C_1$- to $C_2$-alkylstyrene and/or vinyltoluene and (b) from 0 to 95% by weight of other copolymerizable monoethylenically unsaturated monomers.

Particular preference is given to amphiphilic graft polymers prepared by grafting styrene onto a graft base of poly-N-vinylformamide and then, after the graft polymerization, cleaving off from 5 to 100% of the formyl groups from the graft polymer with the formation of amino groups.

To prepare the graft polymers, styrene, alkylstyrene and/or vinyltoluene are preferably subjected in the presence of the graft base to free-radical polymerization in aqueous solution. A preferred mode of preparation of the graft copolymers is solution polymerization, in which case the polymers employed as graft base are preferably in dissolved form. The graft of styrene and/or alkylstyrene with or without other added monomers is or are then added to the polymer solution, either slowly or all at once, and suspended therein. Examples of suitable solvents for solution polymerization are methanol, ethanol, isopropanol, n-propanol, n-butanol, sec-butanol, tetrahydrofuran, dioxane and mixtures of said inert solvents. Solution polymerization in water or in water/alcohol mixtures is preferred. Graft copolymerization can be conducted continuously or batchwise.

The graft copolymers are generally prepared using free-radical initiators. Suitable such initiators are preferably all those which at the chosen polymerization temperature have a half-life of less than 3 hours. If the polymerization is started at a low temperature and completed at a higher temperature, then it is judicious to operate with at least two initiators, which To prepare the graft polymers, styrene, alkylstyrene and/or vinyltoluene are preferably subjected in the presence of the graft base to free-radical polymerization in aqueous solution. A preferred mode of preparation of the graft copolymers is solution polymerization, in which case the polymers employed as graft base are preferably in dissolved form. The graft of styrene and/or alkylstyrene with or without other added monomers is or are then added to the polymer solution, either slowly or all at once, and suspended therein. Examples of suitable solvents for solution polymerization are methanol, ethanol, isopropanol, n-propanol, n-butanol, sec-butanol, tetrahydrofuran, dioxane and mixtures of said inert solvents. Solution polymerization in water or in water/alcohol mixtures is preferred. Graft copolymerization can be conducted continuously or batchwise.

The graft copolymers are generally prepared using free-radical initiators. Suitable such initiators are preferably all those which at the chosen polymerization temperature have a half-life of less than 3 hours. If the polymerization is started at a low temperature and completed at a higher temperature, then it is judicious to operate with at least two initiators, which decompose at different temperatures, i.e. first to employ an initiator which decomposes at a relatively low temperature, to start the polymerization, and then to bring the principal polymerization to an end using an initiator that decomposes at a higher temperature. Both water-insoluble and water-soluble initiators, or mixtures thereof, can be employed. The water-insoluble initiators are then soluble in the organic phase. For example, the initiators listed below can be used for the temperature ranges indicated.

Temperature: 30–60° C.:

Acetylcyclohexanesulfonyl peroxide, diacetyl peroxydicarbonate, dicyclohexyl peroxydicarbonate, di-2-ethylhexyl peroxydicarbonate, tert-butyl perneodecanoate, 2,2'-azobis(4-methoxy-2,4-dimethylvaleronitrile), 2,2'-azobis(2-methyl-N-phenylpropionamidine) dihydrochloride, 2,2'-azobis(2-methylpropionamidine) dihydrochloride.

Temperature: 60–80° C.:

tert-Butyl perpivalate, dioctanoyx peroxide, dilauroyl peroxide, 2,2'-azobis(2,4-dimethylvaleronitrile).

Temperature: 80–100° C.:

Dibenzoyl peroxide, tert-butyl per-2-ethylhexanoate, tert-butyl permaleate, 2,2'-azobis(isobutyronitrile), dimethyl 2,2'-azobisisobutyrate, sodium persulfate, potassium persulfate, ammonium persulfate.

Temperature: 100–120° C.:

Bis(tert-butylperoxy)cyclohexane, tert-butyl peroxyisopropyl carbonate, tert-butyl peracetate, hydrogen peroxide.

Temperature: 120–140° C.:

2,2-Bis(tert-butylperoxy)butane, dicumyl peroxide, di-tert-amyl peroxide, di-tert-butyl peroxide.

Temperature: >140° C.:

p-Menthane hydroperoxide, pinane hydroperoxide, cumene hydroperoxide and tert-butyl hydroperoxide. If in addition to these initiators use is also made of salts or complexes of heavy metals, for example salts of copper, of cobalt, of manganese, of iron, of vanadium, of nickel and of chromium, or organic compounds, such as benzoin, dimethylaniline or ascorbic acid, then it is possible to reduce the half-lives of the free-radical initiators indicated. Thus, for example, tert-butyl hydroperoxide can be activated with the addition of 5 ppm of copper (II) acetylacetonate such that polymerization can be carried out at just 100° C. The reductive component of redox catalyst can also be formed, for example, by compounds such as sodium sulfite, sodium bisulfite, sodium formaldehyde-sulfoxylate and hydrazine. Based on the monomers employed in the polymerization use is made, for example, of from 0.01 to 20% by weight, preferably from 0.05 to 10% by weight, of a polymerization initiator or a mixture of two or more thereof. As redox components, from 0.01 to 15% of the reductive compounds is added. Heavy metals are employed in proportions in the range of, for example, from 0.1 to 100 ppm, preferably from 0.5 to 10 ppm. It is often advantageous to employ a combination of peroxide, reducing agent and heavy metal as redox catalyst.

Styrene, alkylstyrene and/or vinyltoluene together with any other monomers, in the presence of the graft base having units of the formula I and, if appropriate, II, can also be polymerized under the action of ultraviolet radiation, with or without UV initiators being present. For polymerization under the action of UV rays, the customary photoinitiators and sensitizers are employed, examples being compounds such as benzoin and benzoin ethers, α-methylbenzoin or α-phenylbenzoin. So-called triplet sensitizers, such as benzyl diketals, can also be used. Examples of UV radiation sources include both high-energy UV lamps, such as carbon arc lamps, mercury vapor lamps and xenon lamps, and low-UV light sources, such as fluorescent tubes with a high blue component.

To prepare graft copolymers with a low K value the graft copolymerization is judiciously conducted in the presence of regulators. Examples of suitable regulators are mercapto compounds, such as mercaptoethanol, mercaptopropanol, mercaptobutanol, mercaptoacetic acid, mercaptopropionic acid, butyl mercaptan and dodecyl mercaptan. Other suitable regulators are allyl compounds, such as allyl alcohol, aldehydes, such as formaldehyde, acetaldehyde, propionaldehyde, n-butyraldehyde and isobutyraldehyde, formic acid, ammonium formate, propionic acid, hydrazine sulfate and butenols. If polymerization is conducted in the presence of regulators the amount required of the latter is from 0.05 to 20% by weight, based on the monomers employed in the polymerization.

The graft polymerization is usually conducted at from 20 to 200° C., with or without superatmospheric pressure. The preferred range, however, is from 30 to 120° C.

For reactions conducted in solution it is judicious to choose concentrations of from 5 to 80% by weight, preferably from 10 to 60% by weight.

A preferred preparation technique for the amphiphilic graft polymers is the one-pot technique in which in one reactor first of all the graft base is prepared, then the graft component is added immediately all at once, and then polymerized, or is metered in during the polymerization in accordance with the progress of the reaction.

The graft polymers have K values of from at least 7 to 300, determined in accordance with H. Fikentscher in 5% strength by weight aqueous solution at 25° C. and a pH of 7. The K values of the graft copolymers are preferably in the range from 10 to 200. The stated K values correspond to molar masses $M_w$ of from 200 to 10 million. The molar masses $M_w$ are preferably from 500 to 5 million.

The molar masses $M_w$ were determined with the aid of light scattering.

The amphiphilic graft polymers obtainable in this way are used as strength enhancers for paper, as fixing agents for water-soluble and water-insoluble contaminants in papermaking, as dispersants for organic and inorganic pigments, dyes, concrete and crop protection agents, as a detergent additive, as floor care compositions, as a protective colloid for aqueous polymer dispersions, as thickeners for cosmetics formulations, as conditioners for skin care compositions and as a constituent of cosmetic hair preparations and of cosmetic preparations for oral care.

When used in detergents, the amphiphilic graft copolymers act as a grayness-inhibiting (antiredeposition) additive, promote the soil release effect during washing, and inhibit color transfer.

The parts stated in the examples are by weight. The K values were determined in accordance with H. Fikentscher, Cellulose-Chemie, Volume 13, 58 to 64 and 71 to 74 (1932) at 25° C., a pH of 7 and under the concentrations indicated respectively in the examples. The molar masses Mw were determined by the method of light scattering.

EXAMPLES

Graft Base A

A vessel of capacity 2 l was charged with 823 g of water, 7.69 g of 85% strength phosphoric acid and 6.72 g of 50% strength aqueous sodium hydroxide solution. The pH is 6.5. The vessel is evacuated, setting a pressure of initially 600 mbar and subsequently 500 mbar. The contents of the vessel are heated to 80° C. 245 g of N-vinylformamide (feedstream 1) are metered in over the course of 2 hours and 1.8 g of 2,2'-azobis(2-methylpropionamidine) dihydrochloride, dissolved in 117 g of water (feedstream 2), are metered in over the course of 3 hours, at 80° C. After the end of the feed the reaction mixture is stirred at 80° C. for 3 hours more. Over the entire reaction period a total of 149 g of volatile components are distilled off, which are condensed. An aqueous solution is obtained having a solids content of 24.4%. The K value of poly-N-vinylformamide is 63.3 (measured in 1% strength aqueous solution). The molar mass $M_w$ is 70,000.

Graft Base B

A vessel of capacity 2 l is charged with 100 g of water, 2.8 g of 75% strength phosphoric acid and 1.9 g of 50% strength aqueous sodium hydroxide solution. The pH of the solution is 6.5. The aqueous solution is heated under nitrogen to 73° C. and the pressure is established at 350 mbar. Then 200 g of N-vinylformamide (feedstream 1) are metered in over the course of 2 hours and a solution of 0.78 g of 2,2'-azobis(2-methylpropionamidine) dihydrochloride in 100 g of water (feedstream 2) is metered in over the course of 3 hours to the aqueous solution that has been heated to 73° C. After the end of the addition of initiator the reaction mixture is polymerized to completion at 73° C. for 3.5 hours more. Over the entire reaction period, volatile components are distilled off from the reaction mixture and condensed. The total amounts [sic] of condensate is 400 g. On cooling, the amount of water removed by distillation is replaced by water. A clear, colorless aqueous solution is obtained having a solids content of 15.5%. The K value of the poly-N-vinylformamide is 84.7 (determined in 0.5% strength aqueous solution). The molar mass $M_w$ of the polymer is 300,000.

Graft Base C

A reactor is charged with an aqueous solution of 1.8 g of $NaH_2PO_4$ in 700 g of water and the aqueous solution is heated under nitrogen to 70° C. When this temperature has been reached, an aqueous solution of 180 g of N-vinylformamide and 20 g of N-vinylcaprolactam is added over the course of 2 hours and an aqueous solution of 1,6 g of 2,2'-azobis(2-methylpropionamidine) dihydrochloride in 50 g of water is added over the course of 3 hours at a uniform rate. The reaction mixture is subsequently stirred at 75° C. for one hour. An aqueous copolymer solution is obtained having a solids content of 17.3%. The K value of the copolymer is 78 (determined at a polymer concentration of 1% in 5% strength aqueous sodium chloride solution). The molar mass $M_w$ of the polymer is 200,000.

Example 1

A reactor fitted with stirrer, reflux condensor and metering devices is charged with 1003.6 g of a 15.5% strength aqueous solution of graft base B and this initial charge is heated under nitrogen to 85° C. When this temperature has been reached, 5.18 g of styrene are added over the course of 3 hours and an aqueous solution of 0.1 g of 2,2'-azobis(2-methylpropionamidine) dihydrochloride in 30 g of water is added over the course of 4 hours at a uniform rate. Following the addition of the initiator the reaction mixture is stirred at 85° C. for another 2 hours. An aqueous solution is obtained of a graft polymer having a solids content of 17%. The K value of the graft polymer is 85.6 (measured in 1% strength aqueous solution), its molar mass $M_w$ is 313,000.
Hydrolysis

Example 1.1

450 g of the aqueous polymer solution obtained in accordance with Example 1 are heated to 80° C. with stirring. 86 g of 50% strength aqueous sodium hydroxide are added over the course of one hour and the reaction mixture is subsequently stirred at 80° C. for 2 hours. It is then cooled and adjusted to a pH of 7 by adding 85 g of concentrated hydrochloric acid. The degree of hydrolysis of the poly-N-vinylformamide grafted with styrene is 100%. The molar mass of the polymer is 200,000.

Example 1.2

400 g of the aqueous solution of the graft polymer obtained in accordance with Example 1 are heated at 80° with stirring. As soon as this temperature has been reached, 57.5 g of 50% strength aqueous sodium hydroxide are added over the course of one hour and the reaction mixture is subsequently stirred at 80° C. for 2 hours. It is then cooled and adjusted to a pH of 7 by adding 57 g of concentrated hydrochloric acid. The degree of hydrolysis of the graft polymer is 75%. The graft polymer has a molar mass $M_w$ of 230,000.

Example 2

In the reactor described in Example 1, 1047 g of a 15.5% strength aqueous solution of the graft base B are heated under nitrogen to 85° C. As soon as this temperature has been reached, 9.0 g of styrene are metered in over the course of 3 hours and an aqueous solution of 0.18 g of 2,2'-azobis(2-methylpropionamidine) dihydrochloride in 30 g of water is metered in over the course of 4 hours at a uniform rate. To complete polymerization of the reaction mixture, 0.5 g of 2,2'-azobis(2-methylpropionamidine) dihydrochloride is then added and the reaction mixture is stirred for 2 hours more at 85° C. An aqueous solution is obtained of a graft polymer having a solids content of 17.2%. The K value of the graft polymer is 85.6 (measured in 1% strength aqueous solution), its molar mass $M_w$ is 325,000.
Hydrolysis

Example 2.1

500 g of the aqueous solution of the graft polymer obtained in accordance with Example 2 are heated to 80° C., and over one hour 97 g of 50% strength aqueous sodium hydroxide are added. The reaction mixture is subsequently stirred for 2 hours, cooled and adjusted to a pH of 7 by adding 99 g of concentrated hydrochloric acid. The degree of hydrolysis of the graft polymer is 100%. The hydrolyzed graft polymer has a molar mass $M_w$ of 212,000.

Example 2.2

477.5 g of the aqueous solution of the graft polymer obtained in accordance with Example 2 are heated to 80° C., and over one hour 69.4 g of 50% strength aqueous sodium hydroxide are added. The reaction mixture is stirred for 2 hours at 80° C., then cooled and adjusted to a pH of 7 by adding 69 g of concentrated hydrochloric acid. The degree of hydrolysis of the graft polymer is 75%. The hydrolyzed graft polymer has a molar mass $M_w$ of 250,000.

Example 3

In the reactor indicated in Example 1, 819.7 g of a 24.4% strength aqueous solution of graft base A are heated under nitrogen to 85° C. At this temperature, 6.0 g of styrene are then added over the course of 3 hours and an aqueous solution of 0.12 g of 2,2'-azobis(2-methylpropionamidine) dihydrochloride in 30 g of water is added over the course of 4 hours at a uniform rate. To complete polymerization, 0.5 g of 2,2'-azobis(2-methylpropionamidine) dihydrochloride is then added and the reaction mixture is subsequently stirred at 85° C. for 2 hours. An aqueous solution is obtained of a graft polymer having a solids content of 23.4% and a molar mass $M_w$ of 74,000.

Example 3.1

430 g of the aqueous solution of the graft polymer placed here [sic] in accordance with Example 3 are heated to 80° C., and 118 g of 50% strength aqueous sodium hydroxide are added over the course of one hour. After adding the sodium hydroxide, the reaction mixture is stirred at 80° C. for 2 hours more, then cooled and adjusted to a pH of 7 by adding 108 g of concentrated hydrochloric acid. The degree of hydrolysis of the graft polymer is 100%. The hydrolyzed graft polymer has a molar mass $M_w$ of 50,000.

Example 3.2

375 g of the aqueous solution of a graft polymer obtained in accordance with Example 3 are heated to 80° C., and 77.3 g of 50% strength aqueous sodium hydroxide are added over the course of one hour. The reaction mixture is subsequently stirred at 80° C. for 2 hours more, then cooled and adjusted to a pH of 7 by adding 75 g of concentrated hydrochloric acid. The degree of hydrolysis of the graft polymer is 75%. The hydrolyzed graft polymer has a molar mass $M_w$ of 75,000.

Example 4

901.6 g of a 24.4% strength aqueous solution of graft base A are charged to the reactor described in Example 1 and are heated to 85° C. under nitrogen. At this temperature, 11.0 g of styrene are then added over the course of 3 hours and an aqueous solution of 0.22 g of 2,2'-azobis(2-methylpropionamidine) dihydrochloride in 30 g of water is metered in over the course of 4 hours at a uniform rate. Then 0.5 g of 2,2'-azobis(2-methylpropionamidine) dihydrochloride is added and the reaction mixture is stirred at 85° C. for 2 hours more in order to complete polymerization. An aqueous polymer solution is obtained having a solids content of 23.5%. The molar mass $M_w$ of the graft polymer is 77,000.

Example 4.1

470 g of the aqueous solution of the graft polymer obtained in accordance with Example 4 are heated to 80° C., and 129 g of 50% strength aqueous sodium hydroxide are added over the course of one hour. The reaction mixture is subsequently stirred for 2 hours more, then cooled and adjusted to a pH of 7 by adding 123 g of concentrated hydrochloric acid. The degree of hydrolysis of the graft polymer is 100%. The molar mass $M_w$ of the hydrolyzed graft polymer is 52,000.

Example 4.2

425 g of the aqueous solution of the graft polymer obtained in accordance with Example 4 are heated to 80° C., and 87.6 g of 50% strength aqueous sodium hydroxide are added over the course of one hour. The reaction mixture is subsequently stirred for 2 hours, then cooled and adjusted to a pH of 7 by adding 85 g of concentrated hydrochloric acid. The degree of hydrolysis of the graft polymer is 75%. The molar mass $M_w$ of the hydrolyzed graft polymer is 49,000.

Example 5

In the reactor described in Example 1, 941 g of a 17% strength aqueous solution of graft base B are heated under nitrogen to 85° C. At this temperature, a monomer mixture of 23.58 g of n-butyl acrylate, 5.05 g of styrene and 3.37 g of acrylonitrile is metered in over the course of 3 hours and, separately from this, an aqueous solution of 0.64 g of 2,2'-azobis(2-methylpropionamidine) dihydrochloride in 100 g of water is metered in over the course of 4 hours at a uniform rate. Then 0.3 g of 2,2'-azobis(2-methylpropionamidine) dihydrochloride fills in [sic] and the reaction mixture is stirred at 85° C. for 2 hours more. A white polymer dispersion is obtained having a solids content of 18.1%. The molar mass $M_w$ of the polymer is 357,000.

Example 6

In the reactor described in Example 1, 1123 g of an aqueous solution of graft base B are heated under nitrogen to 60° C. At this temperature 76.8 g of styrene are metered in over the course of 3 hours and 3.0 g of a solution of 3.0 g of VA 044 in 30 g of toluene are metered in over the course of 4 hours at a uniform rate. Then 0.5 g of VA 044 is added to the reaction mixture which is stirred at 70° C. for 3 hours to complete polymerization. A white polymer dispersion is obtained having a solids content of 16%. The polymer has a molar mass $M_w$ of 230,000.

Example 7

In the reactor described in Example 1, 491.3 g of a 17.3% strength aqueous solution of graft base C are heated under nitrogen to 85° C. As soon as this temperature has been reached, 9 g of styrene are metered in over the course of 3 hours and an aqueous solution of 0.18 g of 2,2'-azobis(2-methylpropionamidine) dihydrochloride in 30 g of water is metered in over the course of [lacuna] hours at a uniform rate. 0.3 g of 2,2'-azobis(2-methylpropionamidine) dihydrochloride is then added to the reaction mixture, which is stirred at 85° C. for 2 hours to complete polymerization. A white polymer dispersion is obtained having a solids content of 18.7%. The molar mass $M_w$ of the polymer is 239,000.

Performance Examples

The copolymers are added in papermaking, as fixing agents for contaminants, in amounts of from 0.30 to 1.5%, based on pulp, to the paper suspension. As a measure of the fixing performance, the optical transmission of the filtrate is measured. The following polymers were tested:
Polymer 1: the styrene-grafted polyvinylformamide, 75% hydrolyzed, prepared in accordance with Example 1.2.
Polymer 2: prepared in accordance with Example 4.1.
Polymer 3: polydiallyldimethylammonium chloride having a molar mass $M_w$ of 200,000 (prior art comparison).
Polymer 4: customary commercial, water-soluble polymer of high molecular mass based on modified polyethyleneimine (Catiofast SF); prior art comparison.

Example 8

An aqueous fiber slurry of TMP (thermomechanical pulp) with a concentration of 2% was divided into equal portions, to each of which was added an aqueous solution of 5% humic acid as contaminant. Samples of this pulp were each treated with the amounts of polymer 1 indicated in Table 1 and, in addition, with the same amount of a customary commercial, cationic polyacrylamide of high molecular mass as flocculant. The absorbance of the filtrate at 340 nm is determined after thorough mixing and filtration of the flocculated pulp.

TABLE 1

| Fixing agent employed | Amount of polymer, based on pulp [%] | Absorbance of the filtrate at 340 nm |
|---|---|---|
| Examples according to the invention | | |
| a) Polymer 1 | 0.30 | 0.793 |
| b) Polymer 1 | 0.50 | 0.470 |
| c) Polymer 1 | 0.80 | 0.256 |
| d) Polymer 1 | 1.00 | 0.193 |
| e) Polymer 1 | 1.25 | 0.183 |
| f) Polymer 1 | 1.50 | 0.129 |
| Comparison examples | | |
| a) Polymer 3 | 0.00 | 1.087 |
| b) Polymer 3 | 0.30 | 0.549 |
| c) Polymer 3 | 0.50 | 0.284 |
| d) Polymer 3 | 0.80 | 0.222 |
| e) Polymer 3 | 1.00 | 0.214 |
| f) Polymer 3 | 1.25 | 0.189 |
| g) Polymer 3 | 1.50 | 0.167 |

Example 9

An aqueous fiber slurry of TMP (thermomechanical pulp) with a concentration of 2% was divided into equal portions, to each of which was added an aqueous solution of A) 0.2% wood extract, B) 5% humic acid and C) 15% ligninsulfonate as contaminant. Samples of this pulp were each treated with the amounts of test polymer indicated in Table 2 and, in addition, with the same amount of a customary commercial, cationic polyacrylamide of high molecular ass as flocculant. The absorbance of the filtrate at 340 nm is determined after thorough mixing and filtration of the flocculated pulp.

TABLE 2

| Fixing agent employed | Amount of polymer based on pulp [%] | Absorbance of the filtrate at 340 nm contaminant | | |
|---|---|---|---|---|
| | | A | B | C |
| Examples according to the invention | | | | |
| a) Polymer 1 | 0.30 | 0.434 | 0.656 | 0.831 |
| b) Polymer 1 | 0.50 | 0.428 | 0.266 | 0.796 |
| c) Polymer 1 | 0.80 | 0.311 | 0.163 | 0.857 |
| d) Polymer 1 | 1.00 | 0.297 | 0.139 | 0.561 |
| e) Polymer 1 | 1.25 | 0.236 | 0.123 | 0.411 |
| f) Polymer 1 | 1.50 | 0.227 | 0.118 | 0.304 |
| Comparison examples | | | | |
| a) Polymer 3 | 0.00 | 0.515 | 1.087 | 0.821 |
| b) Polymer 3 | 0.30 | 0.411 | 0.549 | 0.882 |
| c) Polymer 3 | 0.50 | 0.373 | 0.284 | 0.880 |
| d) Polymer 3 | 0.80 | 0.332 | 0.222 | 0.871 |
| e) Polymer 3 | 1.00 | 0.310 | 0.214 | 0.855 |
| f) Polymer 3 | 1.25 | 0.283 | 0.189 | 0.847 |
| g) Polymer 3 | 1.50 | 0.266 | 0.167 | 0.411 |

Example 10

An aqueous fiber slurry of TMP (thermomechanical pulp) with a concentration of 2% was divided into equal portions, to each of which was added an aqueous solution of a) [sic] 0.2% wood extract, B) 5% humic acid and C) 15% ligninsulfonate as contaminant. Samples of this pulp were each treated with the amounts of test polymer indicated in Table 3 and, in addition, with the same amount of a customary commercial, cationic polyacrylamide of high molecular mass as flocculant. The absorbance of the filtrate at 340 nm is determined after thorough mixing and filtration of the flocculated pulp.

TABLE 3

| Fixing agent employed | Amount of polymer based on pulp [%] | Absorbance of the filtrate at 340 nm contaminant | | |
|---|---|---|---|---|
| | | A | B | C |
| Examples according to the invention | | | | |
| a) Polymer 2 | 0.30 | 0.442 | 0.642 | 0.862 |
| b) Polymer 2 | 0.50 | 0.425 | 0.396 | 0.854 |
| c) Polymer 2 | 0.80 | 0.375 | 0.191 | 0.853 |
| d) Polymer 2 | 1.00 | 0.318 | 0.132 | 0.850 |
| e) Polymer 2 | 1.25 | 0.291 | 0.112 | 0.788 |
| f) Polymer 2 | 1.50 | 0.264 | 0.109 | 0.352 |
| Comparison examples | | | | |
| a) Polymer 4 | 0.00 | 0.561 | 1.162 | 0.862 |
| b) Polymer 4 | 0.30 | 0.484 | 0.511 | 0.972 |
| c) Polymer 4 | 0.50 | 0.426 | 0.224 | 0.853 |
| d) Polymer 4 | 0.80 | 0.393 | 0.175 | 0.797 |
| e) Polymer 4 | 1.00 | 0.382 | 0.131 | 0.718 |
| f) Polymer 4 | 1.25 | 0.301 | 0.110 | 0.311 |
| g) Polymer 4 | 1.50 | 0.200 | 0.111 | 0.289 |

We claim:

1. An amphiphilic graft copolymer comprising: a pre-formed graft base polymer comprising at least 5% by weight based on the total weight of the graft base polymer of units of the formula

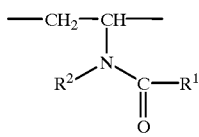

(I)

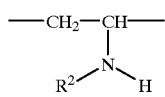

(II)

grafted with at least one monomer selected from the group consisting of styrene, a $C_1$- to $C_2$-alkylstyrene and vinyltoluene and optionally other monoethylenically unsaturated monomers copolymerizable therewith, wherein the ratio by weight of said preformed graft base polymer to said monomer is from 1:99 to 99:1, and at least 5 mole % of the group

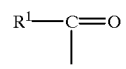

is cleaved off from the graft polymer thereby forming amino groups, and $R^1$ and $R^2$ are H or $C_1$- to $C_6$-alkyl.

2. The amphiphilic graft copolymer of claim 1, wherein said pre-formed graft base polymer comprises at least one polymer selected from the group consisting of a homopolymer of N-vinylformamide and a copolymer of N-vinylformamide and N-vinylcaprolactam.

3. The amphiphilic graft polymer of claim 1, wherein said monomer is styrene and said graft base polymer is poly-N-vinylformamide.

4. A process for preparing the amphiphilic graft polymer of claim 1, which comprises grafting under free-radical conditions at least one monomer selected from the group consisting of styrene, a $C_1$- to $C_2$-alkylstyrene and vinyltoluene and optionally other monoethylenically unsaturated monomers copolymerizable therewith in the presence of pre-formed graft base polymers comprising at least 5% by weight of units of the formula (I), wherein the weight ratio of said monomers to said pre-formed graft base polymer is from 1:99 to 99:1, and cleaving off at least 5 mole % of the group

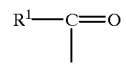

is cleaved from the vinylcarboxamide units of the formula (I), thereby forming amino groups.

5. The process of claim 4, wherein said reacting is conducted in aqueous solution.

6. An aqueous solution or dispersion comprising the amphiphilic graft polymer of claim 1.

7. The solution or dispersion of claim 6, wherein said solution or dispersion further comprises paper fibers.

8. The aqueous solution or dispersion of claim 6, wherein said aqueous solution or dispersion further comprises at least one material selected from the group consisting of organic pigments, inorganic pigments, organic dyes, and inorganic dyes.

9. The aqueous solution or dispersion of claim 6, wherein said aqueous solution or dispersion further comprises concrete.

10. The aqueous solution or dispersion of claim 6, wherein said aqueous solution or dispersion further comprises crop protection agents.

11. The aqueous solution or dispersion of claim 6, wherein said aqueous solution or dispersion further comprises detergent.

* * * * *